United States Patent [19]

Hillstead

[11] Patent Number: 5,019,085
[45] Date of Patent: * May 28, 1991

[54] APPARATUS AND METHOD FOR PLACEMENT OF A STENT WITHIN A SUBJECT VESSEL

[75] Inventor: Richard A. Hillstead, Hollywood, Fla.

[73] Assignee: Cordis Corporation, Miami Lakes, Fla.

[ * ] Notice: The portion of the term of this patent subsequent to Apr. 3, 2007 has been disclaimed.

[21] Appl. No.: 484,693

[22] Filed: Feb. 23, 1990

Related U.S. Application Data

[63] Continuation of Ser. No. 262,831, Oct. 25, 1988, Pat. No. 4,913,141.

[51] Int. Cl.⁵ .............................................. A61B 17/00
[52] U.S. Cl. .................................... 606/108; 606/198
[58] Field of Search ............... 606/108, 109, 139, 198, 606/194

[56] References Cited

U.S. PATENT DOCUMENTS 4,503,569 3/1985 Dotter .
4,776,337 10/1988 Palmaz .
4,913,141 4/1990 Hillstead ............................ 606/108

FOREIGN PATENT DOCUMENTS 2135585 11/1983 United Kingdom .

Primary Examiner—Michael H. Thaler
Attorney, Agent, or Firm—Watts, Hoffmann, Fisher & Heinke Co.

[57] ABSTRACT

A stent delivery system and method. A stent is routed to a desired position within a vessel within a subject. A delivery wire is routed out an opening in a delivery catheter and looped over a portion of the stent and then routed back inside the delivery catheter. At an extreme distal end of the stent, the wire again exits the delivery catheter, reengages the stent and is pushed back into the catheter center passageway. This compresses the stent into a form whereby the delivery catheter can be maneuvered through a vessel to position the stent. To release the stent from the delivery catheter, the delivery wire is retracted so that its distal end passes out both pair of openings in the delivery catheter allowing the stent to expand into engagement with the vessel wall.

7 Claims, 2 Drawing Sheets

APPARATUS AND METHOD FOR PLACEMENT OF A STENT WITHIN A SUBJECT VESSEL

This is a continuation of co-pending application No. 07/262,831 filed on Oct. 25, 1088 now U.S. Pat. No. 4,913,141.

TECHNICAL FIELD

The present invention relates to method and apparatus for positioning an endoprosthesis device within a body vessel, typically a blood vessel.

BACKGROUND ART

A type of endoprosthesis device, commonly referred to as a stent, is placed or implanted within a blood vessel for treating stenoses, strictures, or aneurysms in the blood vessel. These devices are implanted within the vascular system to reinforce collapsing, partially occluded, weakened, or abnormally dilated sections of the blood vessel. Stents also have been successfully implanted in the urinary tract or the bileducts to reinforce those body vessels.

One common procedure for implanting the endoprosthesis or stent is to first open the region of the vessel with a balloon catheter and then place the stent in a position bridging the weakened portion of the vessel.

Prior art patents refer to the construction and design of both the stent as well as the apparatus for positioning the stent within the vessel. One representative patent is U.S. Pat. No. 4,140,126 to Chaudhury which issued Feb. 20, 1979. This patent discloses a technique for positioning an elongated cylinder at a region of an aneurysm to avoid catastrophic failure of the blood vessel wall. The '126 patent discloses a cylinder that expands to its implanted configuration after insertion with the aid of a catheter.

A second prior art patent to Dotter, U.S. Pat. No. 4,503,569 which issued Mar. 12, 1985 discloses a spring stent which expands to an implanted configuration with a change in temperature. The spring stent is implanted in a coiled orientation and heated to cause the spring to expand.

U.S. Pat. No. 4,733,665 to Palmaz which issued Mar. 29, 1988 discloses a number of stent configurations for implantation with the aid of a catheter. The catheter includes a mechanism for mounting and retaining the vascular prosthesis or stent, preferably on an inflatable portion of the catheter. The stent is implanted by positioning it within the blood vessel and monitoring its position on a viewing monitor. Once the stent is properly positioned, the catheter is expanded and the stent separated from the catheter body. The catheter can then be withdrawn from the subject, leaving the stent in place within the blood vessel.

One difficulty in implanting the prosthesis or stent devices of the prior art is the inability to partially position the stent within the blood vessel in an expanded form and determine the appropriateness of the insertion prior to withdrawal of the catheter that delivers the stent. As the stent expands into contact with the blood vessel, it is discharged or separated from the catheter. Removal of an improperly positioned stent must be done surgically by an attending physician. It is accordingly one object of the invention to achieve a stent delivery method and apparatus which allows the stent or prosthesis to be positioned within the blood vessel and the appropriateness of the positioning monitored prior to separation of the stent from the insertion catheter.

DISCLOSURE OF THE INVENTION

The present invention utilizes a two-piece stent insertion system having a delivery catheter and a wire for releasing the stent in a controlled manner.

In accordance with the invention the catheter has an elongated body or wall that terminates at a distal end and defines a passageway extending from a proximal position outside the subject to a distal end of the catheter. The elongated catheter has a stent delivery portion proximal of the distal end having four openings arranged in two pairs. These pairs are spaced by a distance approximately the same as the axial dimension of the stent. A stent retainer is formed from an elongated wire long enough to be inserted down the catheter's passageway to the proximal end and routed outside the catheter through one opening and looped over the stent. The wire is then routed back into the catheter and along the passageway to the vicinity of a third opening where it is again routed outside the catheter's passageway to loop over a distal end of the stent. The wire is then inserted back into the catheter and the stent thereby held compressed against the catheter wall as it is delivered to a desired position.

To position the stent within the body, the catheter is inserted and progress of the stent within the blood vessel or other body passageway is monitored on a viewing screen. When the stent is positioned within a bridging relationship of an area of blood vessel weakness or enlargement, the stent is released at the bridging position. This is accomplished by withdrawing the wire from the catheter a distance sufficient to free one end of the stent. The stent then is free to expand into an uncompressed state even though the wire still engages the stent at its proximal end. If in the physician's opinion, the stent has been properly positioned, continued withdrawal of the wire from the catheter completely frees the stent from the catheter and the catheter is withdrawn. If, however, the stent is improperly positioned, the wire can be held in place to retain the stent as both catheter and stent are withdrawn from the subject.

The disclosed delivery system reduces the possibility of damage to the vessel wall as the stent is positioned and allows an improperly placed stent to be withdrawn with minimal vessel trauma. Different stent designs can be implanted using the disclosed system.

From the above it is appreciated that one object of the invention is a method and apparatus for positioning an expandable stent by selective engagement of that stent through a wire and catheter system which will be explained in more detail in conjunction with the following drawings.

BEST MODE FOR CARRYING OUT THE INVENTION

Figure 1:
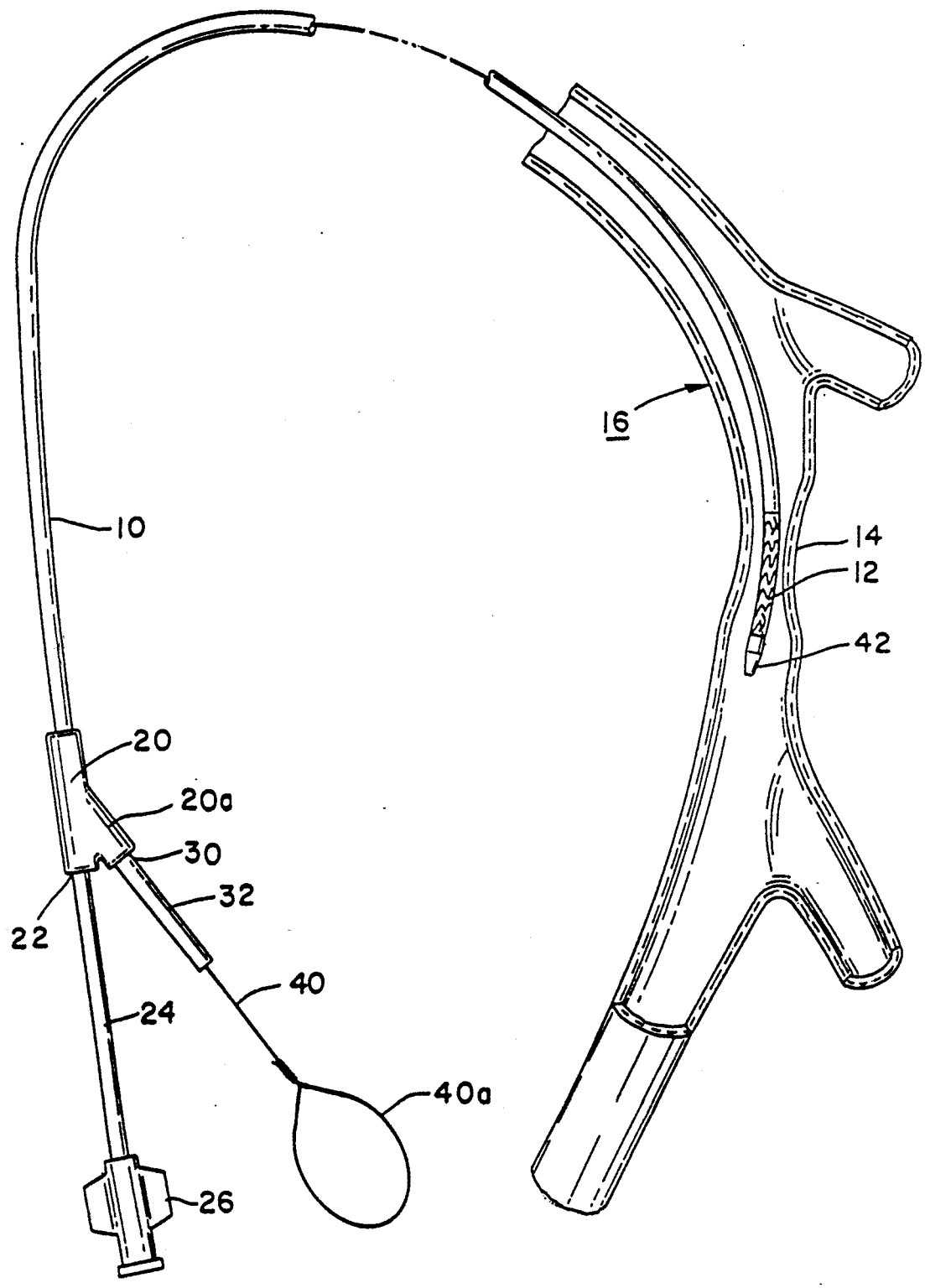
FIG. 1 is a schematic depiction of a stent delivery system constructed in accordance with the invention.

Turning now to the drawings, FIG. 1 shows a catheter 10 for delivering a flexible elongated stent 12 to a weakened region 14 of a blood vessel 16. Techniques are well known within the prior art for catheter insertion and positioning within a patient or subject. During this process, an attending physician monitors progress of the catheter on a fluoroscope which presents a visual image of the catheter as the catheter is routed into the patient. In a typical procedure the catheter 10 is guided to the position shown in FIG. 1 with the help of a guide catheter having a length somewhat less than the length of the catheter 10. Only the distal few inches of the catheter 10 extend beyond the guide catheter.

At a proximal end of the catheter 10, a bifurcating adapter 20 has a single outlet port in fluid communication with the catheter 10. An in-line inlet port 22 supports an inlet tube 24 and leur fitting 26. The fitting 26 is used for injecting fluids through a center passageway 44 (FIG. 2) in the catheter or alternately can be used to apply suction to the center passageway.

A side branch 20a defines a side inlet 30 which supports a second tube 32 having an opening for insertion of an elongated flexible wire 40 which is preferably a stainless steel band. The extreme distal end of the catheter 10 has a tapered distal tip 42 to facilitate insertion of the catheter to an appropriate position within the blood vessel.

Figure 2:
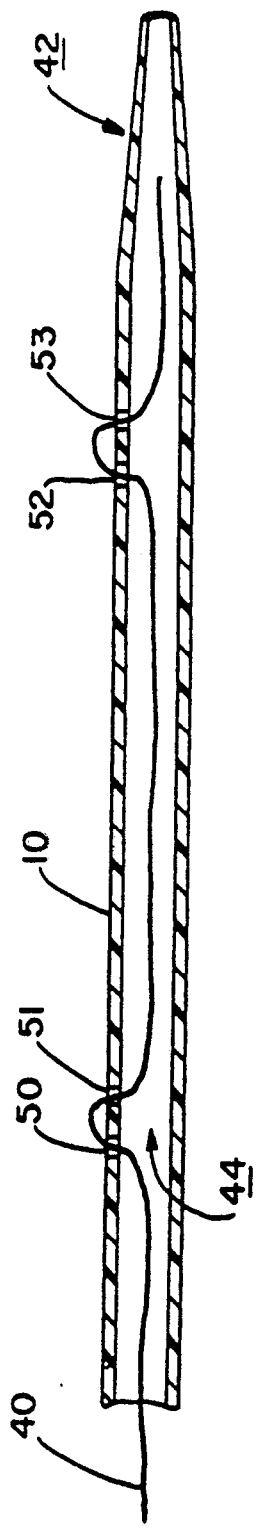
FIG. 2 is a section view through an extreme distal end of a delivery catheter showing a wire for engaging a stent mounted to the catheter.
Figure 3:
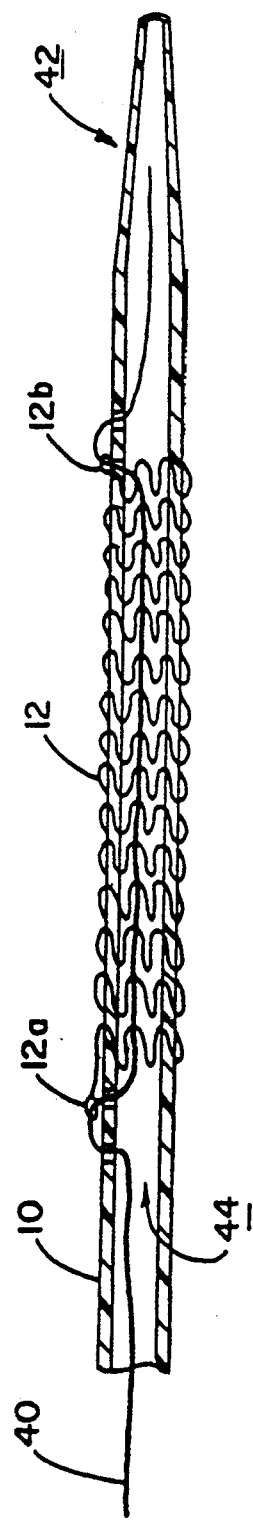
FIG. 3 is a depiction of the FIG. 2 section view with a stent mounted to the catheter.
Figure 4:
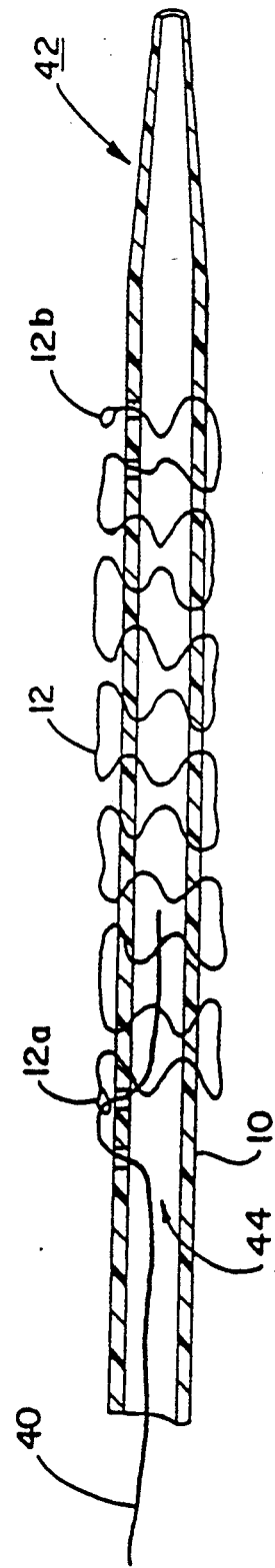
FIG. 4 is a section view of the distal portion of the catheter showing the stent in an expanded configuration subsequent to partial release of the stent within a blood vessel by withdrawal of a stent retaining wire.

The catheter 10 is specially constructed for insertion of the stent 12. As depicted in FIGS. 2 through 4, the catheter 10 has a generally cylindrical shape and defines a single center passageway 44 which extends from the bifurcating adapter 20 to the distal tip 42 and opens into the vessel 16 beyond the distal tip to allow suctioning as well as introduction of a fluid through the catheter to the vessel 16. The center passageway 44 also accommodates a narrow guidewire (not shown) used in positioning the catheter 10. The present invention also has use with a dual lumen catheter having two separate passageways extending through the catheter from a proximal to a distal end. In a dual lumen catheter the wire 40 is routed down a specified one of the two passageways of such a catheter.

The elongated wire 40 is of a length sufficient to allow the wire to be pushed into the tube 32 and routed along the passageway 44 to the distal end of the catheter. The wire 40 preferably comprises a narrow band which is flexible enough to easily follow the tortuous path the catheter 10 may follow as it is inserted through its guide catheter.

As seen most clearly in FIG. 2, the catheter wall is disrupted at two places along the distal end of the catheter. Four openings 50-53 are arranged in two pairs spaced from each other by a length approximately equal to the length of the stent 12 in its compressed state. The openings 50-53 are large enough to accommodate the delivery wire 40 and in a preferred embodiment the openings 50-53 are narrow slits formed in an aligned fashion as depicted in FIG. 2.

Prior to positioning the catheter 10 within the subject, the stent 12 is mounted to the catheter by routing the wire 40 out a first opening 50 and stitched through a loop 12a formed in the stent 12. The stent is fabricated in accordance with techniques disclosed in co-pending U.S. patent application Ser. No. 240,000 filed Sept. 1, 1988 entitled "Radially Expandable Endoprosthesis and the like" which is assigned to the Corvita Corporation. Briefly, the stent comprises a series of continuous corrugations compressed together to form a tube-like mesh of a desired length. Since the stent 12 comprises a single wire, at either end of the stent, the wire can be easily bent to form a loop such as the loop 12a shown in FIG. 3. The stent 12 is slipped over the catheter to a position depicted in FIG. 3 so that the wire 40 can be routed out the opening 50, through the loop 12a, and back into a center passageway 44 through the second opening 51. This effectively secures one end of the stent 12 to the catheter 10.

The wire 40 is then routed through the passageway 44 to the vicinity of the second pair of openings 52, 53. The wire 40 is routed out the opening 52 and through a second loop 12b formed at the extreme distal end of the stent 12. The wire is then pushed back into the catheter through the opening 53 and pushed further into the catheter toward its distal end 42. The wire 40 engages the stent 12 at its extreme proximal and distal ends and is compressed to define a tubular diameter only slightly greater than the diameter of the catheter at this proximal region.

During implantation of the stent, a guide catheter is first positioned within the subject to enable the physician to route the placement catheter 10 to a desired subject location. The placement catheter 10 extends beyond the distal tip of the guide catheter and in particular, the stent 12 is positioned in relation to the region 14 of the blood vessel exhibiting signs of degradation and/or weakness.

Once the delivery catheter 10 has been properly inserted to position the compressed stent (FIG. 3) relative the blood vessel, the wire 40 is partially withdrawn or retracted by the attending physician. This is accomplished by grasping a loop 40a at the extreme proximal end of the wire 40 and withdrawing the wire 40 in a controlled fashion. This withdrawal can be monitored on the viewing screen so that the wire 40 is separated from the stent's distal loop 12b but remains in contact with the stent's proximal loop 12a. Once, the distal loop is disengaged, however, the spring characteristics of the stent cause the stent to expand radially outward, hopefully into engagement with the weakened region 14 of the blood vessel 16. This outward movement of the stent can also be followed on the viewing screen so that the accuracy with which the stent is placed can be carefully monitored.

If the stent is properly positioned to the physician's satisfaction the wire 40 is more fully retracted and pulled through the catheter 10 until the wire 40 passes out the opening 51 and back into the catheter via the opening 50. The proximal loop 12a is then separated from the catheter and the catheter is withdrawn back in the guiding catheter leaving the stent 12 within the vessel. In the event, however, the physician is dissatisfied with the placement of the stent, the wire 40 will not be withdrawn, but instead the catheter 10 and attached stent 12 are pulled back into the guide catheter and removed from the patient.

The preferred stent comprises a series of corrugations that expand outwardly when the delivery wire 40 releases the stent. Other embodiments of the stent from those shown in the drawings are possible so long as these embodiments allow the delivery wire 40 to fix the alternate stent design to the catheter in a compressed form and allows the stent to expand outwardly into engagement with the blood vessel wall once the delivery wire 40 partially releases the stent. Specialty Stents can be used. These may include stents having geometries incorporating intentional irregularities intended to accommodate branches and bifurcating without creating excessive turbulence or disrupting laminar blood flow. It is the intent that the invention include all modifications and alterations from the specific embodiments of the invention disclosed in the drawings falling within the spirit or scope of the appended claims.

I claim:

1. A method for placing a flexible, generally cylindrical wire mesh stent within a blood vessel comprising the steps of:
    (a) mounting the stent to a distal end of an elongated catheter by (i) passing a wire through a passageway of said catheter to an opening in the sidewall of the catheter; (ii) routing the wire out the catheter through the opening to loop over a proximal portion of the stent and returning the wire to the passageway in the catheter; (iii) passing the wire distally to an additional opening in the catheter; and (iv) routing the wire out the additional opening over a distal end of the stent and back into the catheter passageway;
    (b) inserting the elongated catheter into a subject to move the stent to a placement position within the blood vessel; and
    (c) partially releasing the stent by withdrawing the wire from the catheter to release the distal portion of the stent form the wire;
    (d) monitoring the partially released stent on a monitor screen; and
    (e) retracting the stent from the blood vessel by withdrawing said catheter wire and attached stent from the subject.

2. Apparatus for placing a flexible, generally cylindrical, expandable stent within a blood vessel comprising:
    an elongated catheter having a catheter throughpassageway which extends from a proximal end to a distal end of said elongated catheter; said elongated catheter having a stent delivery portion proximal of said distal end defined by spaced apart openings which extend from the catheter throughpassage through a catheter wall; and
    only a single flexible elongated stent retainer for insertion into the catheter passageway to extend from the proximal end of the catheter to the openings in the delivery portion of the catheter where said single stent retainer passes through the catheter wall via said openings to engage said stent and couple the stent to the catheter as the stent is maneuvered within the blood vessel;
    said single flexible elongated stent retainer being retractable to release only one end of said stent once the stent is positioned within the blood vessel and allow the stent to contact inner walls of the blood vessel.

3. A method for positioning a stent within a subject blood vessel comprising the steps of:
    connecting a stent to a catheter with a flexible stent retainer that extends along the catheter to a stent support portion of the catheter and engages the stent at two or more spaced stent engagement positions;
    inserting the catheter and attached stent into a subject and moving the stent to a target region of the subject blood vessel;
    partially releasing the stent by manipulating the flexible stent retainer from outside the subject to separate the stent from the stent retainer at one or more stent engagement positions while maintaining an engagement between the stent and flexible stenty retainer at one or more stent engagement positions; and
    retracting the stent from the target region of the blood vessel by retracting the catheter and flexible stent retainer;
    said step of partially releasing the stent allowing the stent to contact an inner wall of the blood vessel at the target region.

4. The method of claim 3 wherein the step of connecting the stent to the catheter compresses the stent into an insertion configuration and the step of partially releasing the stent allows the stent to expand into engagement with the inner wall of the blood vessel.

5. The method of claim 3 wherein the catheter has a plurality of spaced apart openings that extend through a catheter wall at a distal end of the catheter and wherein the connecting step is performed by:
    (i) routing the flexible stent retainer along a center throughpassage in the catheter to the region of the spaced apart openings, and
    (ii) routing the flexible stent retainer from the center throughpassage via the spaced apart holes to engage the stent at two or more spaced stent engagement positions.

6. A method for positioning a stent within a subject vessel comprising the steps of:
    connecting a stent to a catheter with a flexible stent retainer that extends along the catheter to a stent support portion of the catheter and engages the stent at two or more spaced stent engagement positions;
    inserting the catheter and attached stent into a subject and moving the stent to a target region of the of the subject vessel;
    partially releasing the stent by manipulating the flexible stent retainer from outside the subject to separate the stent form the stent retainer at one or more stent engagement positions while maintaining an engagement between the stent and flexible stent retainer at one or more stent engagement positions; and
    retracting the stent from the target region of the vessel by pulling the catheter, stent and the flexible stent retainer from the subject vessel;
    said step of partially releasing the stent allowing the stent to contact an inner wall of the vessel at the target region.

7. The method of claim 6 wherein the catheter has a plurality of spaced openings that extend through the catheter at a distal end of the catheter and wherein the connecting step is performed by (i) routing the flexible stent retainer along a center through passage in the catheter to the regions of the spaced openings, and (ii) routing the flexible stent retainer from the center through passage via the spaced holes to engage the stent at two or more spaced stent engagement positions.

* * * * *